(12) United States Patent
Bishay et al.

(10) Patent No.: US 6,272,385 B1
(45) Date of Patent: Aug. 7, 2001

(54) INDEPENDENTLY DEPLOYABLE SEALED DEFIBRILLATOR ELECTRODE PAD AND METHOD OF USE

(75) Inventors: Jon M. Bishay, Woodinville; Christine Janae, Seattle, both of WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/145,168

(22) Filed: Sep. 1, 1998

(51) Int. Cl.[7] ................................................ A61N 1/04
(52) U.S. Cl. ............................................. 607/142; 600/392
(58) Field of Search .................................. 607/142, 115, 607/152, 153, 149; 600/372, 386, 391, 392, 395

(56) References Cited

U.S. PATENT DOCUMENTS

| | | |
|---|---|---|
| 4,419,998 | 12/1983 | Heath . |
| 4,483,103 | 11/1984 | Bickel . |
| 4,653,503 | 3/1987 | Heath . |
| 4,681,112 | 7/1987 | Jones et al. . |
| 4,852,585 | 8/1989 | Heath . |
| 4,895,169 | 1/1990 | Heath . |
| 4,955,381 | 9/1990 | Way et al. . |
| 4,979,517 | 12/1990 | Grossman et al. . |
| 5,080,099 | 1/1992 | Way et al. . |
| 5,137,458 | 8/1992 | Ungs et al. . |
| 5,150,708 | * 9/1992 | Brooks ................................. 607/142 |
| 5,330,526 | 7/1994 | Fincke et al. . |
| 5,352,315 | 10/1994 | Carrier et al. . |
| 5,466,244 | 11/1995 | Morgan . |
| 5,571,165 | 11/1996 | Ferrari . |
| 5,984,102 | * 11/1999 | Tay ............................................ 607/5 |

* cited by examiner

*Primary Examiner*—Kennedy Schaetzle
(74) *Attorney, Agent, or Firm*—Cecily Ann Snyder

(57) ABSTRACT

This invention relates generally to medical electrode systems and, in particular, to an independently deployable sealed defibrillator electrode for use with an automatic or semi-automatic external defibrillator (AED). The invention also relates to the method of use thereof. More specifically, this invention relates to an electrode system comprising an electrode layer and a releasing layer which are hermetically sealed together. Each layer contains a pull-tab or gripper for allowing the user to deploy the electrode in one step by pulling apart the two layers. This invention is also directed to a method of using an electrode system of the invention wherein the electrode is deployed in one step by pulling the electrode layer and the releasing layer apart.

14 Claims, 4 Drawing Sheets

INDEPENDENTLY DEPLOYABLE SEALED DEFIBRILLATOR ELECTRODE PAD AND METHOD OF USE

BACKGROUND OF THE INVENTION

1. Field of the Invention

This invention relates generally to medical electrode systems and, in particular, to an independently deployable sealed defibrillator electrode for use with an automatic or semi-automatic external defibrillator (AED). The invention also relates to the method of use thereof.

2. Description of the Prior Art

One frequent consequence of heart attacks is the development of cardiac arrest associated with heart arrhythmias, such as ventricular fibrillation ("VF"). VF is caused by an abnormal and very fast electrical activity in the heart. During VF the heart cannot pump blood effectively. VF may be treated by applying an electric shock to the patient's heart through the use of a defibrillator. Defibrillation clears the heart of the abnormal electrical activity by creating a momentary asystole, thus giving the heart's natural pacemaker areas an opportunity to restore normal function. Because blood no longer pumps effectively during VF, the chance of surviving a heart attack decreases with time after the attack. Quick response by administering a defibrillating shock as soon as possible after the onset of VF is therefore often critically important.

Increasing the number of potential defibrillator operators who are trained in the proper use of an external defibrillator increases the likelihood that a trained defibrillator operator will be available during an emergency and thus could ultimately reduce the defibrillator deployment time. As the number of potential operators increases, however, the frequency with which each operator uses the skills developed during training decreases. Depending upon the amount of time since the defibrillator operator last used a defibrillator, review of electrode placement instructions will likely be required to determine correct placement of the electrode pads. Failure to apply the electrode pads correctly can reduce the amount of energy that is applied to the myocardium. Misapplied electrodes can allow the current to flow along the chest wall, thus missing the heart, and result in a failure of the defibrillation shock. Reviewing pad placement, while necessary, delays the speed with which defibrillation can be performed on the patient. With every second that passes, the likelihood of successfully restoring the patient's heart to a normal sinus rhythm decreases. Therefore, every step in the deployment and use of a defibrillator that can be streamlined is critical.

One time saving gain has been the development of electrode pads that eliminate the step of attaching electrode pads to the cable, and, for the most part, eliminate the need to untangle the cable. Morgan describes an example of such an electrode system in U.S. Pat. No. 5,466,244 for "Defibrillator Electrode System". Other electrode pad designs are known in the art. However, notwithstanding these improvements, electrode deployment and placement is still the most time consuming and difficult step in using an AED.

Currently available defibrillator electrode pads used with AEDs use two adhesive electrode pads adhered to a liner. Additionally, the electrodes are located within a heat sealed pouch. When the electrode pads are deployed during an emergency, the user must, at a minimum, open the bag and then peel the electrodes off the liner prior to attaching the electrodes to the patient. [See, e.g., Zoll stat.padz™.] Where the liner is not part of the bag, the user must also remove the liner from the bag prior to removing the electrodes. [See, e.g., Heartstream® ForeRunner® electrodes and Physio-Control® Fast-Patch® electrodes.] As a result, a minimum of two to three steps is required to deploy the electrode prior to attaching the electrodes to the victim. The more steps required to deploy the electrodes, the longer the victim must wait for the defibrillating shock.

Another problem with deploying electrodes stems from the fact that they can be awkward to use. For example, the electrodes can fold upon itself requiring the user to spend time unfolding the electrode.

What is needed is an easy to use electrode system that enables a rescuer to quickly and accurately apply the electrode pads to a victim of sudden cardiac arrest.

SUMMARY OF THE INVENTION

This invention is directed to an electrode system comprising an electrode layer and a releasing layer which are hermetically sealed together. Each layer contains a pull-tab or gripper for allowing the user to deploy an electrode on the electrode layer in one step by pulling apart the two layers.

This invention is also directed to a method of using an electrode system of the invention wherein the electrode is deployed in one step by pulling the electrode layer and the releasing layer apart.

DESCRIPTION OF THE PREFERRED EMBODIMENTS

Figure 1:
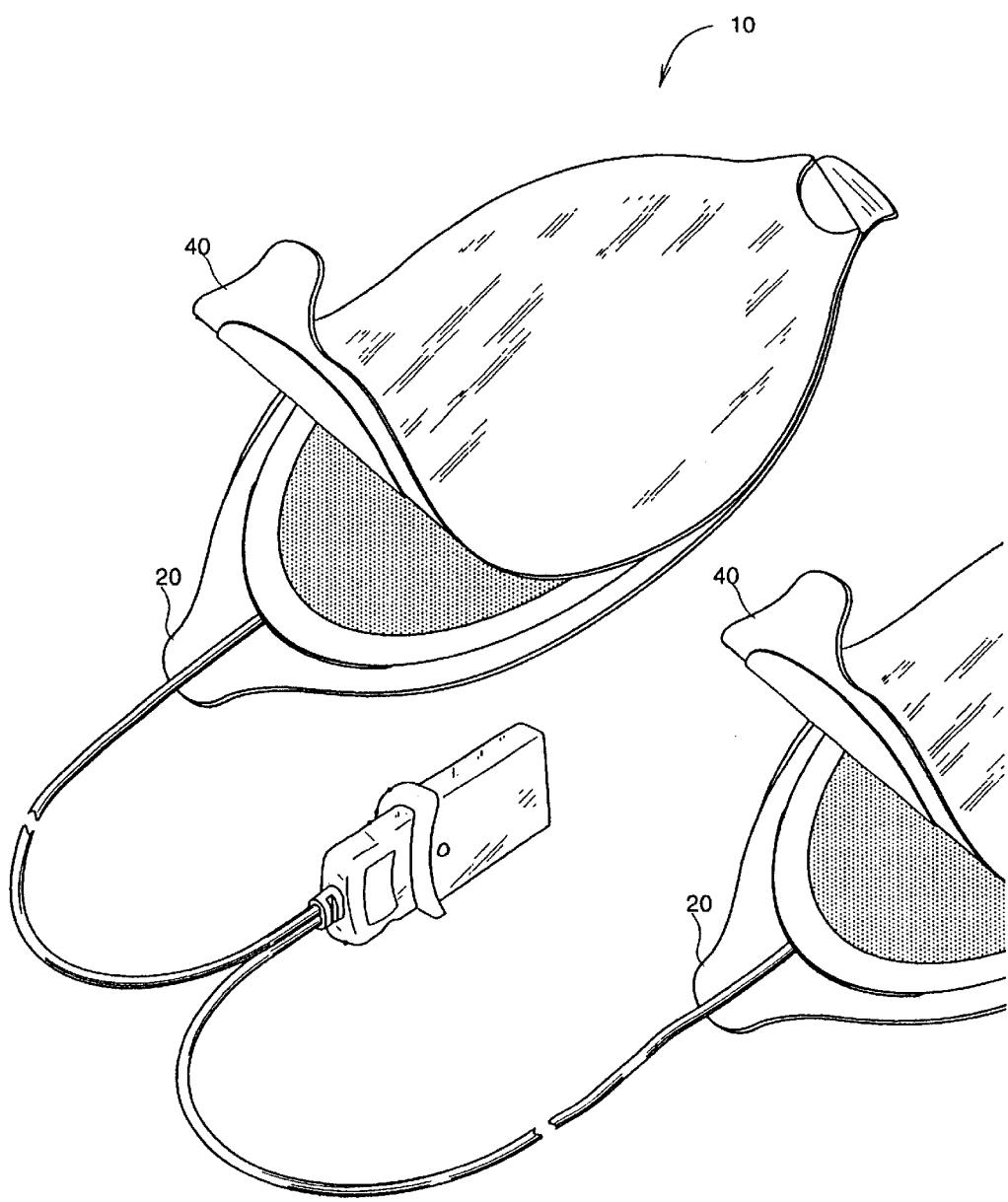
FIG. 1 is a perspective view of an electrode pad system of this invention.

FIG. 1 is a perspective view of an electrode pad system 10 of this invention. The electrode pad system is comprised of two components; the first component being the electrode layer 20 and the second component being the releasing layer 40. The actual construction of the two components is shown in more detail in FIG. 2. An advantage of this two-part construction is that it streamlines the use of the electrode to two steps: deployment and attachment. Thus, the electrode is deployed with one motion prior to applying the electrode to the victim. This construction eliminates additional steps, such as opening the packaging and removing the electrodes prior to applying the electrodes to the victim.

Figure 2:
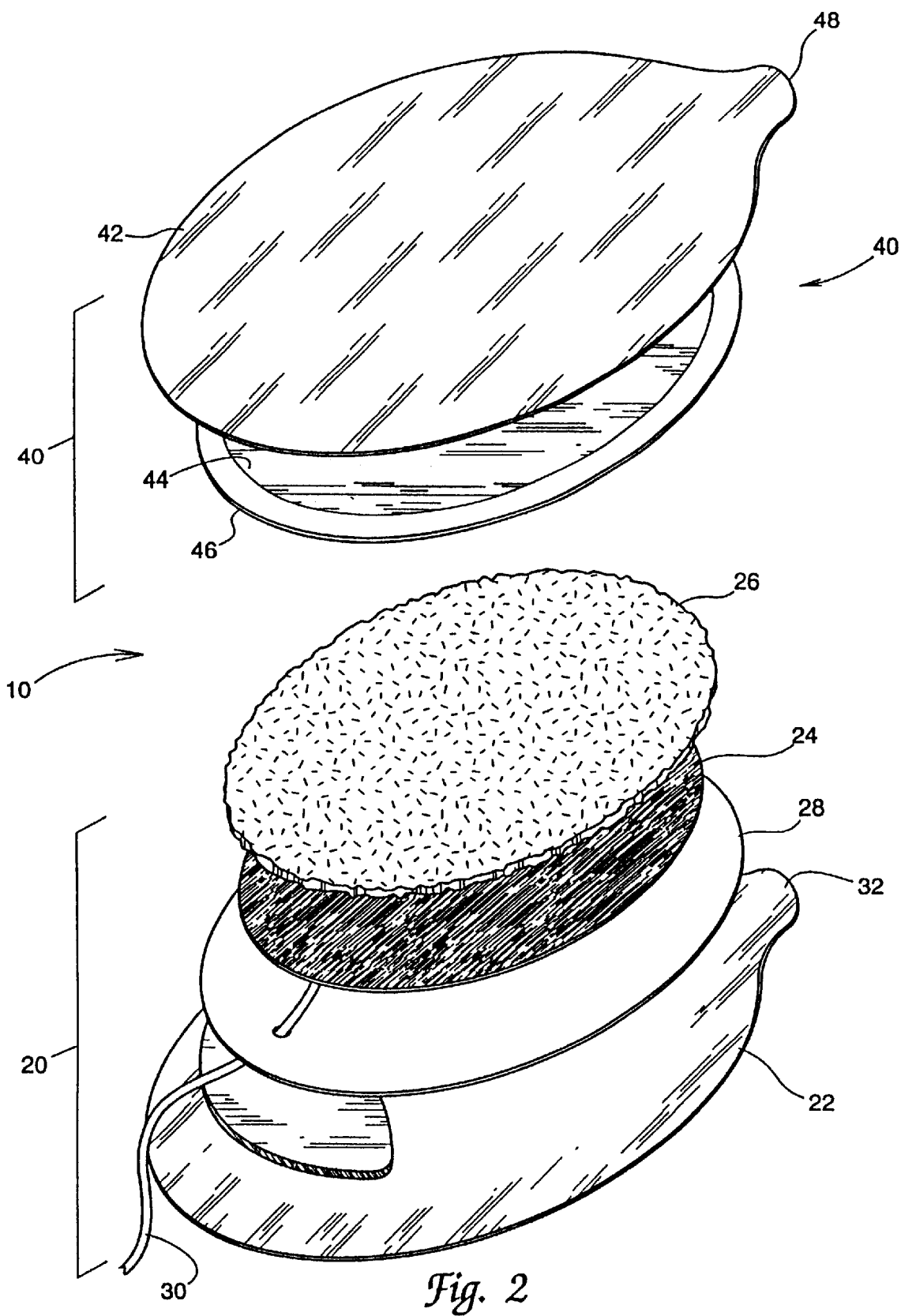
FIG. 2 is an expanded cross-section of the electrode pad 10 shown in FIG. 1.

FIG. 2 is an expanded cross-section of the electrode system 10 shown in FIG. 1. One side of each component (20, 40) forms a non-conductive outer sealing layer (22, 42). In a preferred embodiment, the outer sealing layer is a coated outer sealing layer formed from heat sealing material, such as polyethylene coated polyester or polyethylene coated foil.

The electrode layer 20 is formed from the outer sealing layer 22 adhered to a non-conductive layer 28 with and adhesive layer 34. An electrode disk 24 is adhered to the non-conductive layer of the outer sealing layer using an appropriate adhesive. The electrode disk 24 is formed of a suitable conductive material such as 2 mil tin and is attached to the interior surface of the outer sealing layer 22 with a suitable medical grade adhesive. The electrode disks are electrically connected to a lead wire 30 between the non-conductive sealing layer and the electrode disk on the upper surface of the electrode disk. The lower surface of the electrode disk is covered with a layer of conductive gel 26. A suitable conductive gel would be, for example, RG 63T hydrogel. The conductive gel has adhesive qualities that enable the gel to adhere to the skin of the victim. As will be appreciated by those skilled in the art, other gels may be used without departing from the scope of the invention. Additionally, the electrode layer may be formed so that one end forms a pull tab 32. In a preferred embodiment, the electrode is connected to the lead wire 30 which is connected to an electrode connector (shown in FIG. 1) or directly connected to the defibrillator.

Additionally, the lead wire 30 may be attached to a ring terminal prior to attaching to the electrode disk 24. Further, a washer may be provided between the ring terminal and the electrode disk 24 to improve the electrical connection. Finally, an insulating disk may be provided between the electrode disk 24 and the washer.

The releasing layer 40 is formed from an outer sealing layer 42 which is adhered to a non-conductive layer 46 with the use of an appropriate adhesive 44. In a preferred embodiment, the non-conductive layer is formed of a silicon coated polypropylene impregnated material. The releasing layer 40 is formed so that one end forms a pull tab 48 thus allowing the electrode conductive surface to be exposed with a single pulling motion.

Figure 3:
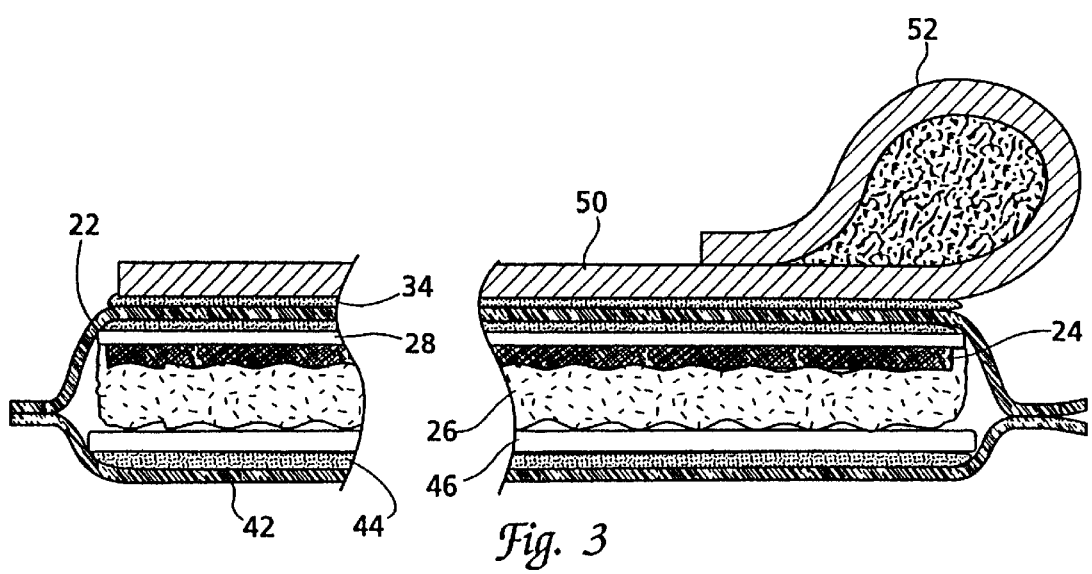
FIG. 3 is cross-section of an alternative embodiment of the electrode pad of FIG. 1 having a gripper 50.

FIG. 3 is a cross-section of an alternative embodiment of the electrode system 10 shown in FIG. 1. In addition to the releasing layer 40 and the electrode layer 20 discussed above with respect to FIG. 2, the electrode system includes a gripper 50 attached to the outer layer of the electrode layer 20 with the use of an appropriate adhesive. The gripper 50 enables the user to firmly grasp the electrode layer 20 while pulling the pull-tab 48 of the releasing layer. The gripper 50 is provided to improve the user's ability to quickly release the electrode layer 20 when deploying the electrode. In the embodiment shown in FIG. 3, the gripper 50 includes a cylindrical grip 52 formed integrally with a flattened section. The flattened side of the gripper 50 is adhered to the outer surface of the sealing layer 22.

Figure 4A:
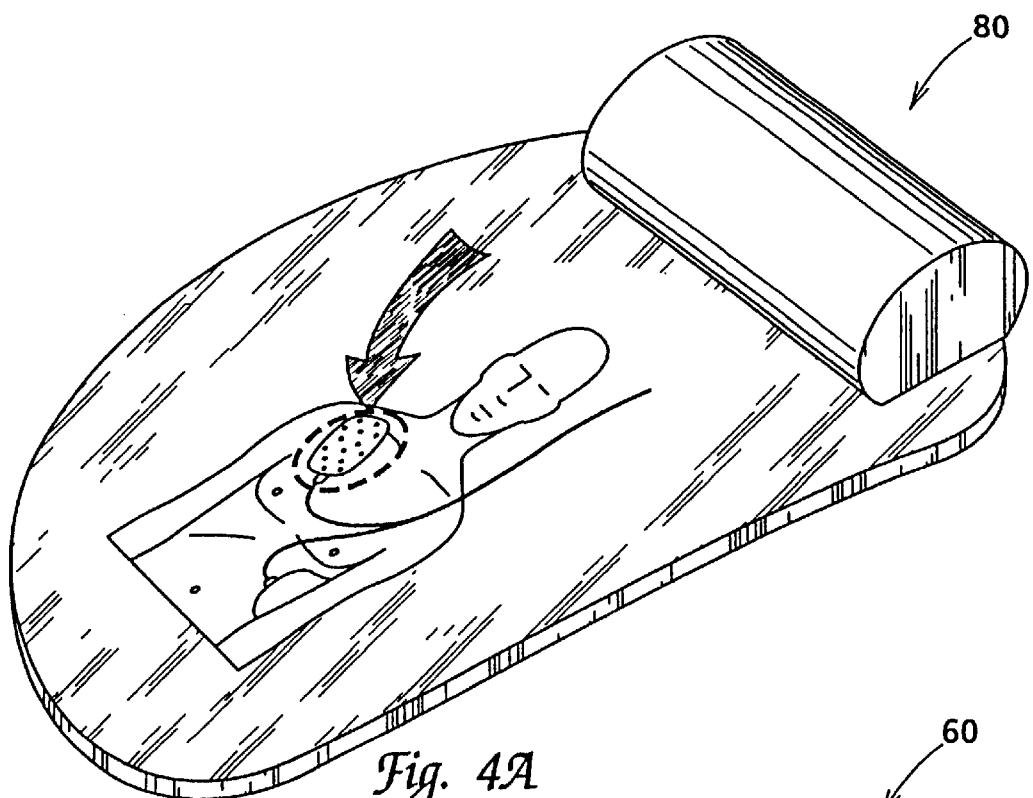
FIG. 4A is a perspective view of the electrode pad shown in FIG. 3.
Figure 4B:
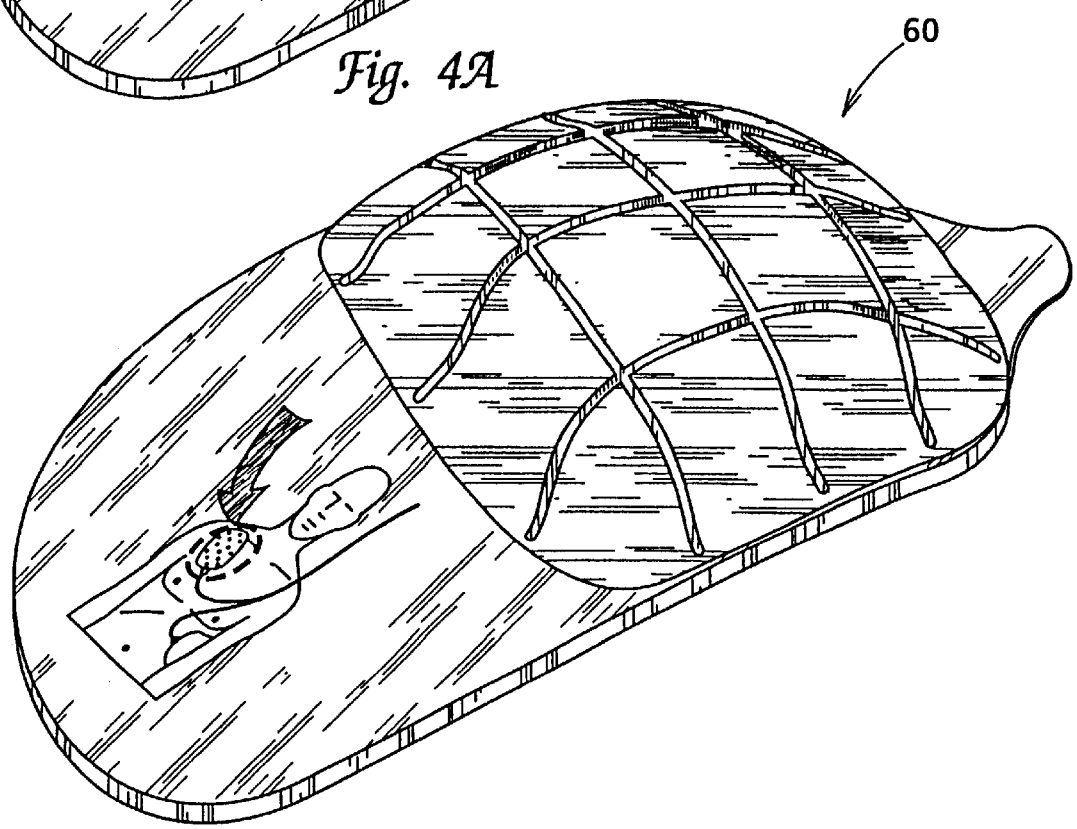
FIG. 4B is a perspective view of an alternate embodiment of the electrode pad shown in FIG. 3.

FIGS. 4A–B shows an alternative embodiment of the electrode system 10 shown in FIGS. 1 and 3. In the embodiment shown in FIG. 4A, the gripper 50 is comprised of a conformable layer 50, 60 that enables the user to firmly and easily grip the electrode layer 20 while removing the releasing layer 40. In a preferred embodiment, the conformable layer is formed of a suitably flexible material, such as medium density polyethylene foam. The conformable layer 50, 60 may also have grooves, or channels, along its length in at least one direction. Alternatively, the conformable layer may be formed from several smaller pieces of foam positioned so that a segmented conformable layer is formed. In a preferred embodiment, the conformable layer 60 is manufactured from a single piece of foam with grooves, or channels, along its length in two directions, as shown in FIG. 4B. In an even more preferred embodiment, the conformable layer 60 is flat on one side thus enabling the conformable layer 60 to adhere to the exterior surface of the sealing layer. The exposed surface of the conformable layer 60 is curved on one side so that it fits within the hand of the user. The conformable layer 60 also improves the user's ability to apply the electrode pad.

In operation of the first embodiment shown in FIG. 1, the user holds the pull tab 28 of the electrode layer 20 in one hand while pulling on the pull tab 48 of the releasing layer 40 with the other hand. Upon pulling the two layers apart, the hydrogel layer 26 is exposed and applied directly to the victim's chest. The actual site of electrode placement will depend upon the protocol followed by the user.

In operation of the second embodiment of the electrode system shown in FIGS. 3, the user grips the gripper 50 in one hand while pulling on the pull tab 48 of the releasing layer 40 with the other hand. As with the previous embodiment, upon pulling the two layers apart, the hydrogel layer 26 is exposed and applied directly to the victim's chest.

In operation of the third embodiment of the electrode system 10 shown in FIGS. 4A–B, the user grips the conformable layer 50, 60 in one hand while pulling on the pull tab 48 with the other hand. Again, upon pulling the two layers apart, the hydrogel layer 26 is exposed and applied directly to the victim's chest.

The embodiments described above are for purposes of illustrating the invention and are not meant to limit the scope of the invention. It is contemplated that various modifications may be made without deviating from the spirit and scope of the invention and will be apparent to persons skilled in the art. All references cited herein are incorporated herein by reference in their entirety.

What is claimed:

1. An electrode comprising,
    an electrode layer having an electrically conductive surface and an environmentally impermeable surface,
    an environmentally impermeable releasing layer; and
    a hermetic seal between the electrode layer and the releasing layer wherein the environmentally impermeable surfaces of the electrode layer and the releasing layer face exteriorly when the layers are sealed together.

2. The electrode system of claim 1 wherein the electrode layer is further comprised of a hydrogel layer and an electrode disk.

3. The electrode system of claim 2 wherein the hydrogel layer is formed from RG 63T hydrogel.

4. The electrode system of claim 2 wherein the electrode disk is a 2 mil tin disk.

5. The electrode system of claim 1 wherein the environmentally impermeable releasing layer is further comprised of a nonstick layer adhered to an electrode facing surface of the releasing layer.

6. The electrode system of claim 1 wherein a gripper is adhered to an exterior facing surface of the environmentally impermeable surface of the electrode layer.

7. The electrode system of claim 6 wherein the gripper is a conformable segmented layer.

8. An electrode system comprising:
    two defibrillation electrodes each connected to a connector by a wire, each defibrillation electrode having an electrode layer having an electrically conductive surface and a substantially environmentally impermeable surface; and a substantially environmentally impermeable releasing layer, wherein the electrode layer and the releasing layer are hermetically sealed.

9. The electrode system of claim 8 wherein the electrode layer is further comprised of a hydrogel layer and an electrode disk adhered to a sealing layer.

10. The electrode system of claim 9 wherein the hydrogel layer is formed from RG 63T hydrogel.

11. The electrode system of claim 9 wherein the electrode disk is a 2 mil tin disk.

12. The electrode system of claim 8 wherein the environmentally impermeable releasing layer is further comprised of a nonstick layer adhered to an electrode facing surface of the releasing layer.

13. The electrode system of claim 8 wherein a gripper is adhered to an exterior facing surface of the environmentally impermeable surface of the electrode layer.

14. The electrode system of claim 13 wherein the gripper is a conformable segmented layer.

* * * * *